United States Patent [19]

Fuchigami et al.

[11] 4,248,736

[45] Feb. 3, 1981

[54] FIBROUS ADSORBENT FOR HEMOPERFUSION

[75] Inventors: Yoshio Fuchigami, Okayama; Toshihide Nakashima, Kurashiki, both of Japan

[73] Assignee: Kuraray Co., Ltd., Kurashiki, Japan

[21] Appl. No.: 258

[22] Filed: Jan. 2, 1979

[30] Foreign Application Priority Data

Jan. 18, 1978 [JP]    Japan ................................... 53-4876

[51] Int. Cl.$^3$ .............................................. B01D 11/04
[52] U.S. Cl. .................................. 252/428; 252/444; 210/502; 210/646; 128/214 R
[58] Field of Search ............................... 252/428, 444

[56] References Cited

U.S. PATENT DOCUMENTS

| | | | |
|---|---|---|---|
| 3,053,775 | 9/1962 | Abbott | 252/447 X |
| 3,969,268 | 7/1976 | Fukuda et al. | 252/444 |
| 3,983,053 | 9/1976 | Courtney et al. | 252/428 X |
| 4,076,892 | 2/1978 | Fennimore et al. | 252/428 X |
| 4,118,341 | 10/1978 | Ishibashi et al. | 252/444 X |
| 4,169,051 | 9/1979 | Satoh et al. | 252/428 X |
| 4,171,283 | 10/1979 | Nakashima et al. | 252/428 |

OTHER PUBLICATIONS

Takahashi et al., Artificial Organs, vol. 5, papers presented at the 14th Meeting of the Japanese Society for Artificial Organs and Tissues, p. 123, (1976).
Andrade et al., Trans. Amer. Soc. Artif. Int. Organs, vol. XVII, (1971), pp. 222-228.
Andrade et al., Trans. Amer. Soc. Artif. Int. Organs, vol. XVIII, (1972), pp. 473-485.

*Primary Examiner*—Patrick Garvin
*Attorney, Agent, or Firm*—Barry Kramer

[57] ABSTRACT

A hemoperfusion adsorbent is provided comprising a woven or knitted fibrous carbon adsorbent material having at least one coating thereon of a hydrophilic polymer. The adsorbent carbon fabric is preferably derived from a novolak-type phenolic resin. The hydrophilic polymer will preferably comprise a polymer prepared by the polymerization of at least one monomeric acrylate or methacrylate, preferably with a copolymerizable monomer containing an epoxy moiety.

8 Claims, 6 Drawing Figures

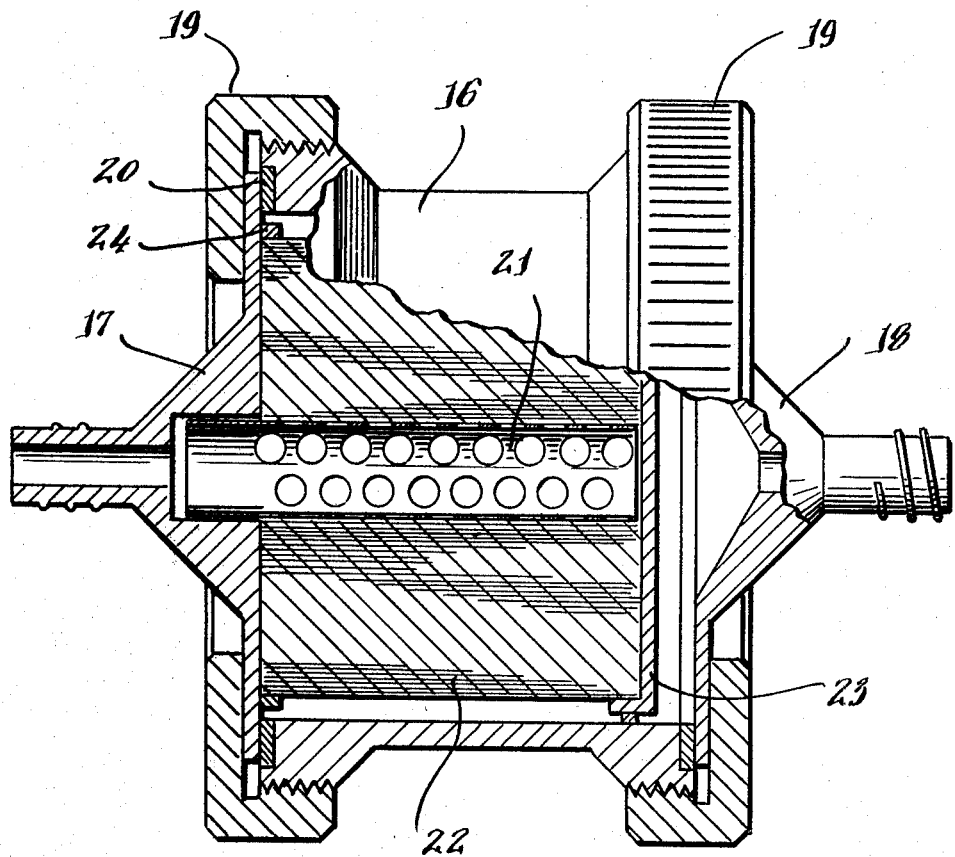

4,248,736

FIBROUS ADSORBENT FOR HEMOPERFUSION

BACKGROUND OF THE INVENTION

This invention relates to an adsorbent for hemoperfusion composed of a fibrous structure of activated carbon. More particularly, the invention relates to an adsorbent of this type wherein a fibrous structure of activated carbon is coated with at least one layer of film-forming substance compatible with blood.

Removal of poisons, metabolites thereof, toxins and the like by artificial means is effective in the treatment of intoxication due to poisons, hepatic coma due to acute and chronic liver failure, renal insufficiency, and the like. Currently, treatment is accomplished by dialysis using semipermeable membranes. Recently, however, attempts have been made to remove substances such as mentioned above by passing the blood directly through an adsorbent material such as activated carbon.

In such direct hemoperfusion techniques, it is important that the adsorbent used therein does not cause blood coagulation, hemolysis, platelet destruction or any other change in the blood components. It is also important that the adsorbent does not release or discharge any micro particles therefrom.

The active carbon adsorbents conventionally used for industrial purposes, such as active carbon from coconut shell and pelletized active carbon from coal or oil, are far from satisfactory for use in hemoperfusion, because of very easy formation of micro particles.

Recently, however, a spherical bead active carbon has been commercially provided having excellent properties for direct hemoperfusion as compared with conventional active carbons. This bead active carbon is manufactured from petroleum pitch obtained as a by-product from ethylene production by steam cracking of crude oil, and is available commercially in Japan. This bead active carbon has a highly uniform spherical configuration of which particle diameter is not more than 1 mm, has a sharp distribution of the diameters, and has a very high abrasion resistance, making it especially suitable for direct hemoperfusion. It is important to employ carbon particles with a diameter of less than 1 mm because the rate of adsorption in the liquid phase depends primarily on the apparent surface area of the adsorbent. Hence, the adsorption rate of an adsorbent having a small apparent surface area is low however large the BET surface area thereof may be. This is because the diffusion coefficient of a substance in the liquid phase is generally a thousandth to a ten-thousandth as small as that in the gaseous phase, and therefore the rate of bulk mass transfer determines the rate of adsorption. On the other hand, when the volume is kept constant, the total apparent surface area is inversely proportional to the bead diameter; accordingly, the smaller the diameter of the bead carbon is, the greater is the rate of adsorption. There is a practical limit, however, on the increased rate of adsorption which can be obtained simply by reducing the bead size. Pressure loss also increases as the diameter decreases, thus there is an optimal diameter from the practical point of view. Thus, for example, it is disclosed in the commonly assigned copending application, U.S. Ser. No. 820,380, filed July 29, 1977 and now U.S. Pat. No. 4,171,283, that a diameter of bead active carbon of 0.5 to 1.0 mm is especially preferable.

This conflict between the rate of adsorption and the pressure loss does not occur when active carbon fibers are used as adsorbents. For fibrous adsorbents, the fiber diameter determines the apparent surface area. Fibers having diameters of from 5 to 100 microns are approximately one-tenth to one-hundredth of that of the preferred bead active carbons, and remarkably increase rates of adsorption. Moreover, because fibers of active carbon can be woven or knitted into a fibrous structure such as a felt or a fabric and used as such, the pressure loss can be controlled independently of the diameter of the fibers. The pressure loss across a fibrous structure can be varied by changing the weight and fabrication of the fibrous structure, as well as the manner of supporting the fibrous structure in a container.

One advantage which results from the greatly increased rate of adsorption permitted by the fibrous structure, is that the break-through curve is very sharp, and it is possible to employ extremely small bed lengths. With the same contact time (absorbent volume in ml/flow rate of blood in ml/hr), the shorter the bed length is, the smaller is the pressure loss. Another advantage of the active carbon fiber adsorbent is that coating or washing of the adsorbent to be described hereinbelow can be carried out after fitting the adsorbent in a column and fixing the same therein.

Though advantages such as mentioned above can be expected from their use, no practical hemoperfusion apparatus has yet been proposed employing active carbon fiber adsorbents. This is probably the result of the following two principal difficulties: first, active carbon fibers present far larger amounts of micro particles than the bead active carbon due to the stripping or falling off of fiber fragments; and secondly, active carbon fibers show an adverse effect toward the blood, especially in causing a marked decrease in the platelet count (Takahashi et al, Artificial Organs, vol. 5, papers presented at the 14th Meeting of the Japanese Society for Artificial Organs and Tissues, page 123, 1976). We believe that one of the causes for such an untoward action is the lack of a blood compatible surface on the conventional active carbon fibers.

SUMMARY OF THE INVENTION

The above problems are effectively solved and other advantages are obtained as set forth in more detail below, by the present invention which provides an adsorbent for hemoperfusion which comprises a woven or knitted fibrous carbon adsorbent structure having at least one coating thereon of a hydrophilic, blood-compatible, film-forming polymer.

BRIEF DESCRIPTION OF THE DRAWINGS

The invention and its advantages will be better understood from the following detailed description, especially when read in conjunction with the following drawings wherein:

FIG. 6 is a side elevational view, partly in section showing a preferred embodiment of a blood purifier containing a fibrous hemoperfusion adsorbent according to the present invention.

DETAILED DESCRIPTION OF THE INVENTION

Figure 1:
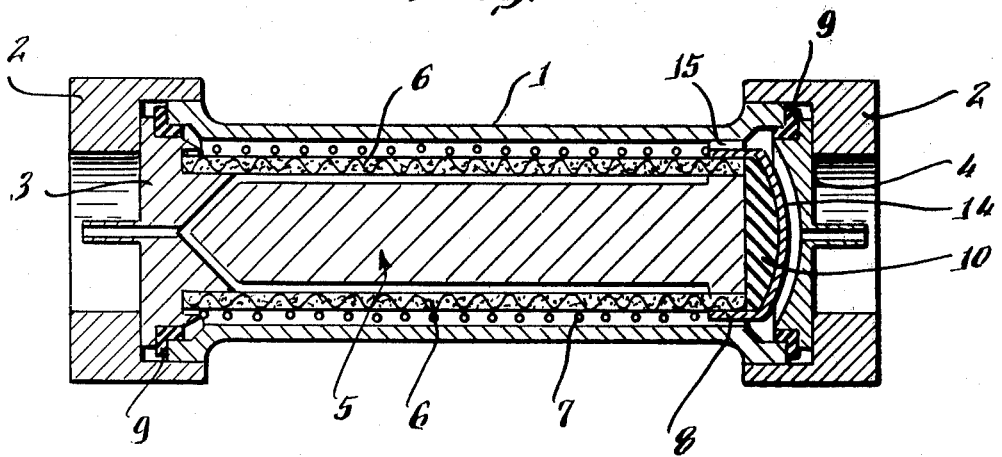
FIG. 1 is a cross-sectional view showing one embodiment of a blood purifier containing a fibrous hemoperfusion adsorbent according to the present invention.

According to the invention, a fibrous active carbon material is coated with at least one layer of a blood-compatible, hydrophilic, film-forming, polymer material. While the invention relates generally to suitable fibrous adsorbents and blood-compatible (hemocompatible) polymers effective for the purposes set forth, the following presents a discussion of several preferred systems.

As a result of the present inventors' investigation as to which kinds of active carbon fibers are usable, it has been found that those active carbons that are derived from fibrous precursors made of regenerated cellulose (e.g. viscose rayon), polyacrylonitrile or novolak-type phenol-formaldehyde resin (hereinafter sometimes called "phenol resin") are preferable. Active carbon fibers prepared from these materials exhibit generally decreased fiber fragment formation during the fabrication of the fibrous structure to be described later, and have favorable adsorbent characteristics. Carbon fibers produced from novolak-type phenol resins are especially preferable for hemoperfusion because of the high rate of adsorption, as shown in the examples.

In accordance with the invention, the active carbon fibers mentioned above are not used as such, but used in the form of a woven or knitted fabric, which is herein called "a fibrous structure". Felts, on the other hand, are not suitable for purposes of the present invention because they do not have high enough bulk densities and they tend to create excessive fiber fragments. Heretofore it has been considered that the blood would tend to be retained in a fibrous structure because of the bulky nature of the structure. This, if true, would cause blood coagulation and render the structure unfit for the intended use. Contrary to this prediction, however, the inventors have found that the fibrous structures of the present invention having hemocompatible coatings thereon, do not cause blood coagulation and have all the advantages of active carbon fibers.

Among the fibrous structures, woven fabrics are preferred because of their high bulk density. For example, a plain-weave active carbon cloth with a weight of 80 grams per square meter shows a bulk density of 0.25 g/cc, which is at least eight times as great as the bulk density of 0.03 g/cc of a felt made of an active carbon fiber. Owing to this, a more compact container can be employed, according to the present invention, for packing the active carbon of a certain quantity as compared with the active carbon of other configurations. This is important not only from the standpoint of compactness of size but also from the standpoint that less volume is required to prime it to make it ready for use.

The fibrous structure of active carbon may be prepared either by subjecting the precursor fiber to weaving or knitting followed by carbonizing the fiber and activating the carbonized fiber or by carbonizing the fiber followed by making the fibrous structure from the carbonized fiber and activating the same.

Conveniently, the fibrous structure is packed or inserted in a vessel or container therefor in the form of a roll. Where this is intended, a woven cloth with a predetermined width made of an active carbon fiber can conveniently be taken up by means of an automatic take-up roller. While the pressure loss depends upon the weight of the woven cloth and the roll thickness, the weight of the woven cloth is preferably from 50 to 150 g/m$^2$, and the thickness will suitably be between 1 to 10 cm. With such a fibrous structure, the pressure loss due to the blood flow can be limited to the clinically acceptable range of 40 to 50 mmHg or below.

Active carbon cloths derived from novolak-type phenol resins are most advantageous, because these resins are thermosetting and can be carbonized and activated after making into a fibrous structure having the desired form and size. Active carbon fibers derived from phenol resins of the novolak type are commercially available, for example, from Japan Kynol Co., Ltd. under the trademark "KYNOL" fiber.

The blood-compatible, film-forming substance will comprise a polymer selected from the group consisting of nitrocellulose, cellulose acetate, dextran, hydroxyethylcellulose, polyamide, hydrophilic methacrylate or acrylate polymers, polyvinyl alcohol, gelatin and copolymers or derivatives thereof. Each of these terms is meant to include those modified or derivative forms of any of these wherein albumin, heparin or the like is contained therein in free or chemically bound form. In view of hemocompatibility, however, hydrophilic methacrylate or acrylate polymers are most preferred.

Suitable hydrophilic acrylate and methacrylate polymers are polymers or copolymers which consist essentially of at least one monomer selected from the group consisting of hydrophilic acrylates or methacrylates such as substituted or unsubstituted hydroxy- or alkoxyalkyl acrylates and methacrylates, substituted or unsubstituted amino- or alkylamino-alkyl acrylates and methacrylates, and substituted or unsubstituted poly(alkylene glycol) acrylates and methacrylates, such hydrophilic acrylates and methacrylates being represented by the general formula

$$CH_2=CR_1 \atop | \atop COOY \qquad (I)$$

wherein $R_1$ is hydrogen or methyl; and Y is a radical selected from the group consisting of $-R_2-OR_3$ and $-R_2-NR_3R_3'$, wherein $R_2$ is a divalent alkylene radical containing 2 to 3 carbon atoms or a poly(oxyalkylene) radical, which can be substituted; and $R_3$ and $R_3'$, respectively, are hydrogen or a substituted or unsubstituted alkyl group containing 1 to 3 carbon atoms, the substituent being a polar one such as hydroxyl or amino. Illustrative of such acrylate and methacrylate monomers are hydroxyethyl methacrylate, hydroxyethyl acrylate, hydroxypropyl methacrylate, hydroxypropyl acrylate, polyethylene glycol monomethacrylate, polyethylene glycol monoacrylate, polypropylene glycol monomethacrylate, polypropylene glycol monoacrylate, methoxyethyl methacrylate, methoxyethyl acrylate, dimethylaminoethyl methacrylate and dimethylaminoethyl acrylate.

Coating of the fibrous structure of active carbon with such a hydrophilic acrylate or methacrylate polymer or copolymer prevents adverse effects to the blood due to fiber fluff from falling off. However, polymers with relatively low molecular weights are eluted or dissolved during sterilizing treatments, such as autoclaving, which are necessary for the blood purifier to be used for practical purposes. The polymer fractions which are eluted or dissolved can be determined quantitatively by known methods such as by titration with potassium permanganate. Although thorough washing prior to sterilization can prevent elution, this takes an excessively long period of time and unnecessarily burdens the assembly steps. In order to shorten the time required for the washing step, the coating layer is preferably cured or cross-linked.

According to this more preferred embodiment, the coating material for the active carbon fiber comprises a hydrophilic acrylate or methacrylate copolymer with a minor amount of a curable comonomer component selected from the group consisting of polymerizable monomers containing an epoxy group and having the general formula

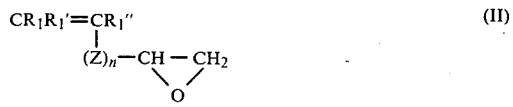

(II)

wherein $R_1$, $R_1'$ and $R_1''$, respectively, are hydrogen or methyl; Z is a divalent radical selected from the group consisting of $-COOR_2-$, and $-CH_2-OCH_2-$; n is 0 or 1; and $R_2$ is a divalent alkylene radical containing 1 to 3 carbon atoms or a poly(oxyalkylene) radical which can be substituted with a polar group such as hydroxyl or amino. Illustrative of such comonomers containing an epoxy moiety are glycidyl methacrylate, glycidyl acrylate, glycidyl crotonate, allyl glycidyl ether, butadiene monoxide, and isoprene monoxide. Glycidyl methacrylate and glycidyl acrylate are especially preferred.

The hydrophilic polymers of use in the present invention can be prepared by copolymerizing a predominant amount of monomer (I) with a minor amount of the epoxy-containing comonomer (II) in a solvent such as methanol, ethanol or dimethylformamide, and in the presence of a free radical polymerization initiator such as azobisisobutyronitrile, diisopropyl peroxydicarbonate, tert-butyl peroctoate or benzoyl peroxide, and the like, at a temperature of 40° to 100° C. for several hours. The amount of the epoxy-containing comonomer (II) is within the range of from 0.1% to 10% based on the weight of the total monomers. A smaller amount will result in insufficient cross-linking effect, while a larger amount will result in insolubilization tendency during storage.

A coating of the hydrophilic polymer is applied to the active carbon as a solution. The polymer is dissolved in a solvent such as methanol or ethanol to make a solution with a concentration of 0.01 to 10%, preferably 0.5 to 5%, and applied to the fibrous structure of active carbon by immersion, spraying, wet coagulation technique, or the like. The treated fibrous structure is first air-dried and then dried in hot air at a temperature of 80° to 120° C. for 1 to 24 hours. When the coating is made with a hydrophilic copolymer of an acrylate or methacrylate monomer with an epoxy-containing comonomer, the epoxy group causes cross-linking at the time of drying, making the copolymer insoluble. As a result, the elution of low molecular weight polymers from the coating layer during sterilization can be prevented almost completely, especially in the autoclaving treatment which is essential for medical use. Moreover, the cross-linked layer produces an excellent effect in preventing fragments of active carbon fiber from falling off. Two or more repetitions of the coating procedure can make the above effects more reliable. After the coating and drying, the fibrous structure is washed with water and then sterilized.

The active carbon is held in a suitable container for use. It is a feature of this invention that the coating, drying, rinsing and sterilizing can be done after the fibrous structure of active carbon is positioned and fixed in the container. This enables simplified automation of all of these steps, making it possible to more economically produce hemoperfusion apparatus in large numbers.

FIG. 1 shows a sectional view of one embodiment of the blood purifier in accordance with the invention. Housing 1 has blood inlet 3 and blood outlet 4 at its respective ends, each mounted thereon with cap 2 for sealing. It is desirable to put packing 9 or the like between the cap and the housing. Blood inlet 3 is coupled separably or unseparably to core 5 for the fibrous structure of active carbon. Fibrous structure 6 of active carbon is mounted on said core 5. If necessary, it is possible to cover fibrous structure 6 with a net 7 or the like in order to effectively protect said fibrous structure of active carbon against possible damage at the time of insertion into the housing, and to maintain an appropriate clearance between the housing wall and the fibrous structure. The terminal portion of core 5 can be given any desired shape through the use of sealing member 10 or the like.

Figure 2:
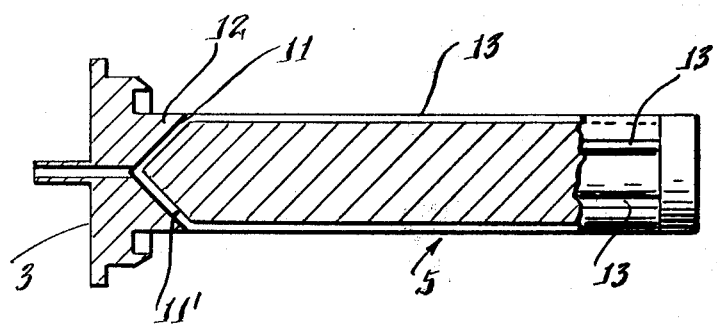
FIG. 2 shows the detail of a core for supporting the fibrous adsorbent in the blood purifier shown in FIG. 1.
Figure 3:
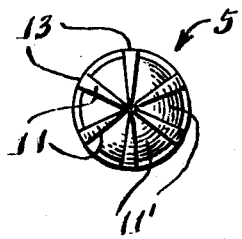
FIG. 3 is an end view of the core shown in FIG. 2, showing the detail of the blood distribution channels at the inlet end.

FIG. 2 shows an example of core 5 for the fibrous structure of active carbon. Blood inlet 3 and core 5 contact at surfaces 11 and can either be bonded together with an adhesive applied to the contact surfaces 11, or can be coupled to each other by other means, such as grooving and fitting. FIG. 3 shows an end view core 5 seen from the inlet side. A plurality of ridges 11 are provided on the cone-shaped end of said core 5, and these ridges come in contact with concavity 12 of inlet 3. Clearances 11' between ridges 11 serve as blood distributors. The cylindrical surface of the core 5 also has ridges 13 which are the continuations of ridges 11. The blood is led from the clearances on the conical surface to clearances between ridges 13 arranged on the cylindrical surface of core 5.

Figure 4:
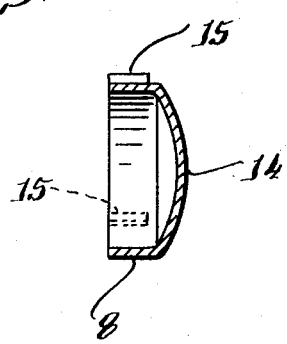
FIG. 4 is a cross-sectional view of a cover for fitting over the outlet end of the core shown in FIG. 2.
Figure 5:
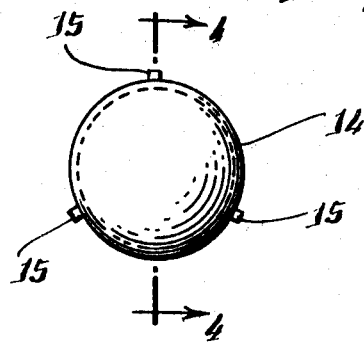
FIG. 5 is a right side elevational view of the cover shown in FIG. 4.

In normal construction, the edge of the fibrous structure 6 is gathered at both ends of core 5. This may cause the blood to be unfavorably retained thereabout. To alleviate this problem, it is desirable to seal the end of core 5 with a sealing member such as shown at 10 in FIG. 1, and further to mount cover 8 at the outlet end. The detail of such cover 8 is illustrated better in FIGS. 4 and 5. Cover 8 is fitted over the end portion of core 5. Cover 8 has a sufficient depth to cover or encircle the edge portion of the fibrous structure and has a smooth and round-shaped end. Ridges 15 may be provided on the circumference of the cover so as to ensure the positioning of the cover in relation to the inside wall of the housing.

FIG. 6 shows a more preferred embodiment of the blood purifier in accordance with the invention. Housing 16 has at its respective ends blood inlet 17 and outlet 18 each mounted with cap 19. Packing 20 is put between the inlet 17 and the housing and between the outlet 18 and the housing, respectively. Blood distributor 21 is fixed to the blood inlet portion by threaded engagement or press fit. Active carbon cloth 22 is rolled on the distributor. If necessary, cloth 22 may be covered with a net. The edge portion of the roll of cloth 22 is sealed by means of cover 23 at the outlet end and washer 24 at the inlet end. Preferably, a sealing agent is applied to either or both the cover 23 and the washer 24 to improve their sealing effect with mating surfaces.

Preferably, the fibrous structure of active carbon is so positioned in the purifier that the blood flows perpendicularly to the fibrous structure plane, as in the above examples. However, this manner of positioning is not essential. The important consideration is to position the fibrous structure such that the amount of blood held within the container is kept as small as possible, and unnecessary retention of blood does not occur.

The adsorbent for hemoperfusion in accordance with the present invention can be used in the treatment of intoxication due to poisons, hepatic coma, renal insufficiency, and the like, by direct hemoperfusion or by perfusion of the plasma obtained, for example, by filtration or centrifugation of the blood. The adsorbent can also be used in the prophylaxis or treatment of diseases by removing harmful substances from preserved blood.

It is possible to use some other kind of adsorbent together with the fibrous structure of active carbon in the same container in accordance with the present invention, or to use another device containing another kind of adsorbent in series or in parallel relationship to the device of the present invention. Also, it is of course effective to use the adsorbent of the present invention in combination with some other type of blood purifier, such as a hemodialyzer or hemofilter.

The following examples are for the purpose of illustrating the invention in more detail, but are not to be taken as limiting thereof. Unless otherwise indicated, all parts and percentages are by weight.

EXAMPLES 1 TO 3 AND CONTROL EXAMPLE 1

Three fibrous adsorbents according to the present invention and one employing bead carbon are here prepared and compared for their effectiveness in removing creatinine from aqueous solution. For Examples 1-3, 0.5 grams of each of Kynol ACC activated plain-weave carbon cloth (weight: 130 g/m², from Japan Kynol Co., Ltd.), KF felt (weight: 240 g/m², from Toyobo Co., Ltd.), and ACF felt (weight: 120 g/m², from Toho Beslon Co., Ltd.) employed as the active carbon fibers. For Control Example 1, 0.5 grams of bead activated carbon BAC-MU.L (from Taiyo Kaken Co., Ltd.) was employed. Each specimen was coated with a copolymer of hydroxyethyl methacrylate and glycidyl methacrylate in the manner described hereinafter in Example 5. Thereafter, each specimen was put in a 200 ml-Erlenmeyer flask containing 100 ml of aqueous creatinine (initial concentration: 0.2 g/l) and the flask was shaken at 120 cycles/min. in a water bath at 37° C. The change in creatinine concentration of the solution with a lapse of time was investigated. Based on the time t(hr) which elapsed before the concentration of creatinine had dropped to 1/20 of its initial concentration, the adsorption rate constant $k(hr^{-1})$ was calculated by the following equation:

$k = (2.30 \log 20)/t$

The results are shown in Table 1.

TABLE 1

| Test No. | Active Carbon | $k(hr^{-1})$ |
|---|---|---|
| Example 1 | Kynol Acc plain-weave cloth | 67 |
| Example 2 | Toyobo KF felt | 36 |

TABLE 1-continued

| Test No. | Active Carbon | $k(hr^{-1})$ |
|---|---|---|
| Example 3 | Toho-Beslon ACF felt | 34 |
| Control Example 1 | Taiyo Kaken beads | 4.5 |

EXAMPLES 4 TO 6 AND CONTROL EXAMPLE 2

In these Examples, three fibrous adsorbents are prepared by coating according to the present invention, and compared to an uncoated control. Each of the Examples, including the control, employed the same fibrous adsorbent material, which was Kynol ACC activated plain-weave carbon cloth (weight: 132 g/m², BET surface area 2100 m²/g). Four blood purifying devices were prepared by placing individual 155 mm by 1200 mm swatches (24.6 g) of the fibrous adsorbent material in each of four devices as shown in FIG. 1. The coatings were then applied to the fibrous material in Examples 4-6 as follows: with that of Control Example 2 remaining uncoated:

EXAMPLE 4

Five liters of a 0.5 W/V% solution of polyhydroxyethyl methacrylate in 95% ethanol was circulated through the vessel at a flow rate of 200 ml/min. for 30 minutes and, after drainage, dry $N_2$ gas was passed through the vessel for 5 minutes.

EXAMPLE 5

A mixture of 99.5 parts of hydroxyethyl methacrylate, 0.5 parts of glycidyl methacrylate, 0.1 part of diisopropyl peroxydicarbonate and 700 parts of 95% ethanol was reacted under a nitrogen atmosphere at 60° C. for 8 hours. The resultant copolymer solution was adjusted to a concentration of 0.5 W/V% with 95% ethanol. Five liters of the copolymer solution was passed through the above vessel at 200 ml/min. for 30 minutes and, after drainage, dry $N_2$ gas was passed for 5 minutes.

EXAMPLE 6

Commercial collodion (as dissolved in ethanol/ether) was diluted with ethanol-ether (1:3) to a concentration of 0.5% and five liters of this solution was circulated at a flow rate of 200 ml/min. for 30 minutes. After drainage, dry $N_2$ gas was passed for 5 minutes.

CONTROL EXAMPLE 2—UNTREATED

The support frames on which the Kynol ACC cloths had been set up, were taken out of each of the above four vessels and dried under reduced pressure at 80° C. for 10 hours, and then dried in a current of hot air at 120° C. for an hour.

Each frame with its respective cloth was reset in its vessel, water was introduced at a flow rate of 200 ml/min., and 100 ml of the effluent was recovered as a sample. Samples were taken initially and after passage of 1, 2 and 3 liters of water. The effluent samples were filtered through Millipore ® filters with a pore size of 1.2 microns and the carbon micro particles sized 10 microns or larger were counted under an optical microscope (magnification: ×80). It was found that the carbon micro particles were invariably fiber fragments, the number of which was as given in Table 2.

TABLE 2

| | Number of Micro Particles | | | |
| --- | --- | --- | --- | --- |
| | Example 4 | Example 5 | Example 6 | Control Example 2 |
| The volume of water passed till sampling (l) 0 | 86 | 64 | 125 | 2080 |
| 1 | 2 | 1 | 12 | 36 |
| 2 | 0 | 0 | 1 | 12 |
| 3 | 0 | 0 | 0 | 6 |

To demonstrate the effectiveness of the various coatings to resist elution or dissolution during sterilization, each of the purification vessels prepared in Examples 4 to 6 was filled with physiological saline, sealed and steam sterilized. The steam sterilization was done in an autoclave at 120° C. for 20 minutes. After cooling, the vessels were unsealed and 10 ml of the fill water (200 ml) was pipetted out of each. To each such sample was added 20 ml of 0.01 N-aqueous $KMnO_4$ together with 1 ml of dilute sulfuric acid, and the mixture was boiled for 30 minutes. After cooling, 0.1 g of KI was added and a titration was carried out with 0.01 N-aqueous $Na_2S_2O_3$, using starch as the indicator. A blank test was also run with 10 ml of water and the difference between each test and the blank was calculated. The results set forth in Table 3 illustrate the effectiveness of the cross-linked polymer of Example 5 to resist elution as compared to the coating of uncross-linked methacrylate polymer of Example 4, and the collodion coating of Example 6.

TABLE 3

| | Example 4 | Example 5 | Example 6 |
| --- | --- | --- | --- |
| Amount of titrant (difference from blank) | 1.6 ml | 0.2 ml | 6.5 ml |

EXAMPLE 7

An adsorbent container was prepared as in FIG. 6 and around its distributor was wrapped a Kynol ACC activated carbon cloth, (weight 90 g/m²), 50 mm wide and 7.5 m long. The cloth was coated, dried and sterilized in the same manner as Example 5.

The device was connected to the arterial and venous blood vessels of a dog and the blood was circulated through the vessel at 200 ml/min. for 3 hours. During this period, there were no signs of a reduction in platelet count, hemolysis or clotting.

The above description is for the purpose of explaining the present invention to those skilled in the art, and is meant to include all those obvious modifications and variations thereof which will become apparent upon reading. It is intended that all such modifications and variations be included within the present invention, the scope of which is defined in the following claims.

What is claimed is:

1. An adsorbent for hemoperfusion which comprises a woven or knitted fibrous structure of activated carbon with a bulk density of at least 0.25 g/cc, said activated carbon having been derived from a fibrous precursor selected from the group consisting of regenerated cellulose, polyacrylonitrile and a thermosetting polymer, and having at least one coating thereon of a hydrophilic, blood-compatible, film-forming copolymer prepared by polymerization of at least one monomeric acrylate or methacrylate represented by the formula:

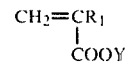

wherein $R_1$ is hydrogen or methyl; and Y is a radical selected from the group consisting of $-R_2-OR_3$ and $-R_2-NR_3R_3'$, wherein $R_2$ is a divalent alkylene radical containing 2 to 3 carbon atoms or a poly(oxyalkylene) radical, and $R_3$ and $R_3'$, respectively, are hydrogen or an alkyl group containing 1 to 3 carbon atoms, with a copolymerizable monomer containing an epoxy radical therein represented by the formula:

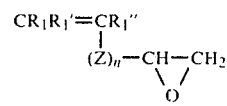

wherein each of $R_1$, $R_1'$, and $R_1''$ independently is hydrogen or methyl; Z is a divalent radical selected from the group consisting of $-COOR_2$ and $-CH_2-OCH_2-$, wherein $R_2$ is a divalent alkylene radical containing 1 to 3 carbon atoms or a poly(oxyalkylene) radical; and n is 0 or 1; the copolymerizable monomer being present therein in the range of from 0.1 to 10% based on the weight of total monomers.

2. An adsorbent according to claim 1 in which the fibrous precursor is a thermosetting polymer.

3. An adsorbent according to claim 1 in which the fibrous structure is woven.

4. An adsorbent according to claim 1 in which the monomeric acrylate or methacrylate is selected from the group consisting of hydroxyethyl methacrylate, hydroxyethyl acrylate, hydroxypropyl methacrylate, hydroxypropyl acrylate, polyethylene glycol monomethacrylate, polyethylene glycol monoacrylate, polypropylene glycol monomethacrylate, polypropylene glycol monoacrylate, methoxyethyl methacrylate, methoxyethyl acrylate, dimethylaminoethyl methacrylate and dimethylaminoethyl acrylate.

5. An adsorbent according to claim 4 in which the monomeric acrylate or methacrylate is hydroxyethyl methacrylate.

6. An adsorbent according to claim 1 in which the copolymerizable monomer is selected from the group consisting of glycidyl methacrylate, glycidyl acrylate, glycidyl crotonate, allyl glycidyl ether, butadiene monoxide, and isoprene monoxide.

7. An adsorbent according to claim 6 in which the copolymerizable monomer is glycidyl methacrylate.

8. An adsorbent according to claim 1 in which the fibrous precursor is a novolak-type phenolic resin.

* * * * *